US012582741B2

(12) United States Patent
Tripodi

(10) Patent No.: US 12,582,741 B2
(45) Date of Patent: Mar. 24, 2026

(54) DEVICE FOR ABATING AIR-BORNE MICROBIOLOGICAL COMPONENTS

(71) Applicant: Paolo Tripodi, Rome (IT)

(72) Inventor: Paolo Tripodi, Rome (IT)

( * ) Notice: Subject to any disclaimer, the term of this patent is extended or adjusted under 35 U.S.C. 154(b) by 265 days.

(21) Appl. No.: 18/274,525

(22) PCT Filed: Jan. 26, 2022

(86) PCT No.: PCT/IB2022/050677
§ 371 (c)(1),
(2) Date: Jul. 27, 2023

(87) PCT Pub. No.: WO2022/162552
PCT Pub. Date: Aug. 4, 2022

(65) Prior Publication Data
US 2024/0316239 A1 Sep. 26, 2024

(30) Foreign Application Priority Data

Jan. 27, 2021 (IT) ........................ 102021000001544

(51) Int. Cl.
*A61L 9/20* (2006.01)
(52) U.S. Cl.
CPC ............. *A61L 9/20* (2013.01); *A61L 2209/11* (2013.01); *A61L 2209/12* (2013.01)
(58) Field of Classification Search
CPC ..... A61L 9/20; A61L 2209/11; A61L 2209/12
See application file for complete search history.

(56) References Cited

U.S. PATENT DOCUMENTS

| | | | |
|---|---|---|---|
| 2019/0015541 A1* | 1/2019 | Peczalski | A61L 9/20 |
| 2024/0337406 A1* | 10/2024 | Lecoffre | F24F 7/06 |
| 2025/0001348 A1* | 1/2025 | Baheux | A61L 9/145 |

FOREIGN PATENT DOCUMENTS

| | | |
|---|---|---|
| CN | 101321992 | 12/2008 |
| CN | 101365532 | 2/2009 |

(Continued)

OTHER PUBLICATIONS

WO 2022/189007 A1 (Year: 2022).*

(Continued)

*Primary Examiner* — Nicole M Ippolito

(57) ABSTRACT

Described herein is a device for abating microbiological components present in an air flow, comprising: a main body, said main body being provided, on its surface, with a first aperture and a second aperture; a plurality of shelves positioned within said main body, each shelf being provided with at least one through hole; a plurality of UV electromagnetic sources arranged between said shelves so as to emit UV light within said main body; a first fan, connected to said first aperture and adapted to suck air into said main body; a control unit configured for driving said plurality of UV electromagnetic sources and said suction fan; wherein said first aperture and said second aperture and each hole of each shelf are in fluidic communication; wherein said main body has a minimum volume $V_{em}$ given by the following relation:

$$V_{em} = D\frac{1}{I}nV$$

where D is the abatement dose necessary for abating a microbiological species by 99%, I is the mean intensity of the electromagnetic field of said plurality of UV electromagnetic sources, and nV is the aeraulic capacity of the device.

10 Claims, 5 Drawing Sheets

(56) References Cited

FOREIGN PATENT DOCUMENTS

| CN | 105964137 | 9/2016 |
| CN | 206320874 | 7/2017 |
| CN | 208275249 | 12/2018 |
| CN | 209967465 | 1/2020 |
| WO | WO 2007/056720 | 5/2007 |
| WO | WO 2007/086726 | 8/2007 |
| WO | WO 2022189007 A1 * | 9/2022 | .............. F24F 13/20 |

OTHER PUBLICATIONS

International Search Report and the Written Opinion Dated Jun. 20, 2022 From the International Searching Authority Re. Application No. PCT/IB2022/050677. (29 Pages).

Communication Pursuant to Article 94(3) EPC Dated May 23, 2025 From the European Patent Office Re. Application No. 22705468.1. (10 Pages).

Communication Pursuant to Article 94(3) EPC Dated Nov. 27, 2025 From the European Patent Office Re. Application No. 22705468.1. (8 Pages).

Notification About Necessity to Submit Additional Materials Dated Oct. 19, 2023 From the Eurasian Patent Organization, The Eurasian Patent Office, EAPO Re. Application No. 202392137 and Its Translation Into English. (4 Pages).

Notification of Office Action and Search Report Dated Nov. 20, 2025 From The State Intellectual Property Office of the People's Republic of China Re. Application No. 202280018422.4 and Its Translation Into English. (13 Pages).

Notification of Substantive Examination Report Dated Oct. 15, 2023 From the Saudi Authority for Intellectual Property Re. Application No. 523450101 and Its Translation Into English. (11 Pages).

Artichowicz et al. "Analysis of the Radiation Dose in UV-Disinfection Flow Reactors", Water, XP093338927, 12(1): 231-1-231-15, Published Online Jan. 11, 2020.

* cited by examiner

DEVICE FOR ABATING AIR-BORNE MICROBIOLOGICAL COMPONENTS

RELATED APPLICATIONS

This application is a National Phase of PCT Patent Application No. PCT/IB2022/050677 having International filing date of Jan. 26, 2022, which claims the benefit of priority of Italy Patent Application No. 102021000001544 filed on Jan. 27, 2021. The contents of the above applications are all incorporated by reference as if fully set forth herein in their entirety.

FIELD AND BACKGROUND OF THE INVENTION

The present invention relates, in general, to the field of devices for air sterilization. In particular, the present invention concerns a device for abating air-borne microbiological components.

As is known, several scientific studies have shown that air-borne microorganisms are sensitive to UV electromagnetic fields.

In particular, the article entitled: "Repair of ultraviolet light induced damage in micrococcus radiophilus, an extremely resistant microorganism", Journal of Bacteriology, 1976; and the article entitled: "Predicted inactivation of viruses of relevance to biodefense by solar radiation", Journal of Virology, 2005, analyze the behaviour of different microbiological species in the presence of a UV electromagnetic field.

Several devices are known which utilize UV electromagnetic fields in order to abate microbiological components.

For example, patent application US 2020/0206375 A1 describes a portable UV-C disinfection apparatus. In particular, said apparatus comprises UV-C emitters coupled to a housing having a planar surface and UV-C sensors configured to measure the amount of UV-C light irradiated onto a target surface. A controller determines the amount of UV-C radiation necessary for disinfecting such surface.

The Applicant perceived the need for providing an alternative UV electromagnetic-wave device that allows achieving air purification.

SUMMARY OF THE INVENTION

The present invention provides a device for abating air-borne microbiological components, comprising:

a main body provided, on its surface, with a first aperture and a second aperture;

a plurality of shelves positioned within said main body, each shelf being provided with at least one through hole;

a plurality of UV electromagnetic sources arranged between said shelves so as to emit UV light within said main body;

a first fan, connected to said first aperture and adapted to suck air into said main body;

a control unit configured for driving said plurality of UV electromagnetic sources and said suction fan;

wherein said first aperture and said second aperture and each hole of each shelf are in fluidic communication.

According to another embodiment, the device further comprises:

a battery adapted to supply power to said suction fan, said plurality of UV electromagnetic sources and said control unit;

a face mask adapted to cover the mouth and/or the nose of a user.

a flexible hose provided with a first end and a second end, wherein:

said first end is connected to said second aperture;

said second end is connected to said face mask.

These and other objects are achieved through the device as described in the appended claims, which are an integral part of the present description.

BRIEF DESCRIPTION OF THE SEVERAL VIEWS OF THE DRAWING

The invention will become more apparent in the light of the following detailed description, supplied merely by way of non-limiting example with reference to the annexed drawings, wherein.

In the drawings, the same reference numerals and letters identify the same or functionally equivalent parts.

Figure 1:
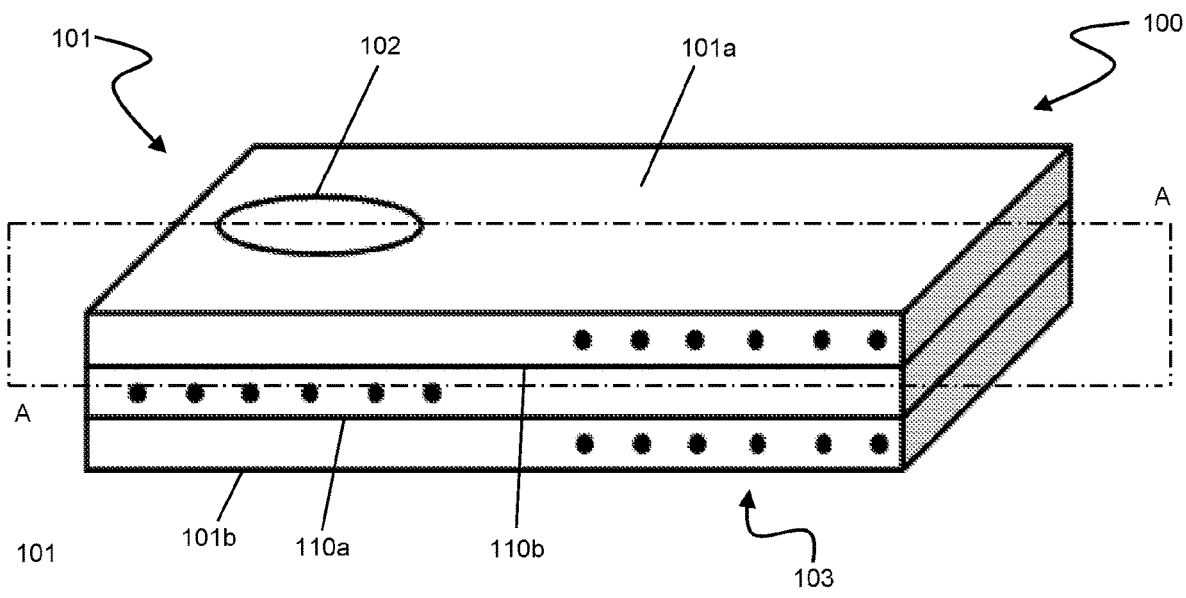
FIG. 1 shows a device for abating air-borne microbiological components according to the present invention.

The figures are provided herein merely for illustrative purposes and are not drawn in scale.

DESCRIPTION OF SPECIFIC EMBODIMENTS OF THE INVENTION

In the following, a device for abating air-borne microbiological components is identified as a whole by reference numeral 100.

With reference to FIG. 1, the device 100 comprises a main body 101. The main body 101 is provided, on its surface, with a first aperture 102 and a second aperture 103.

Preferably, the main body 101 is a box-shaped body having a first surface 101a and a second surface 101b that are substantially parallel to each other. Even more preferably, the first surface 101a and the second surface 101b are substantially flat and parallel to each other.

As an alternative, the main body 101 is a body having a substantially cylindrical shape, with a first surface 101a and a second surface 101b substantially parallel to each other.

Preferably, the first aperture 102 is formed in the first surface 101a and the second aperture 103 is formed in the second surface 101b.

Preferably, the first aperture 102 and the second aperture 103 are substantially circular. Preferably, the first aperture 102 and the second aperture 103 have the same diameter.

Alternatively, the first aperture 102 and the second aperture 103 have different shapes and/or different dimensions.

Figure 2:
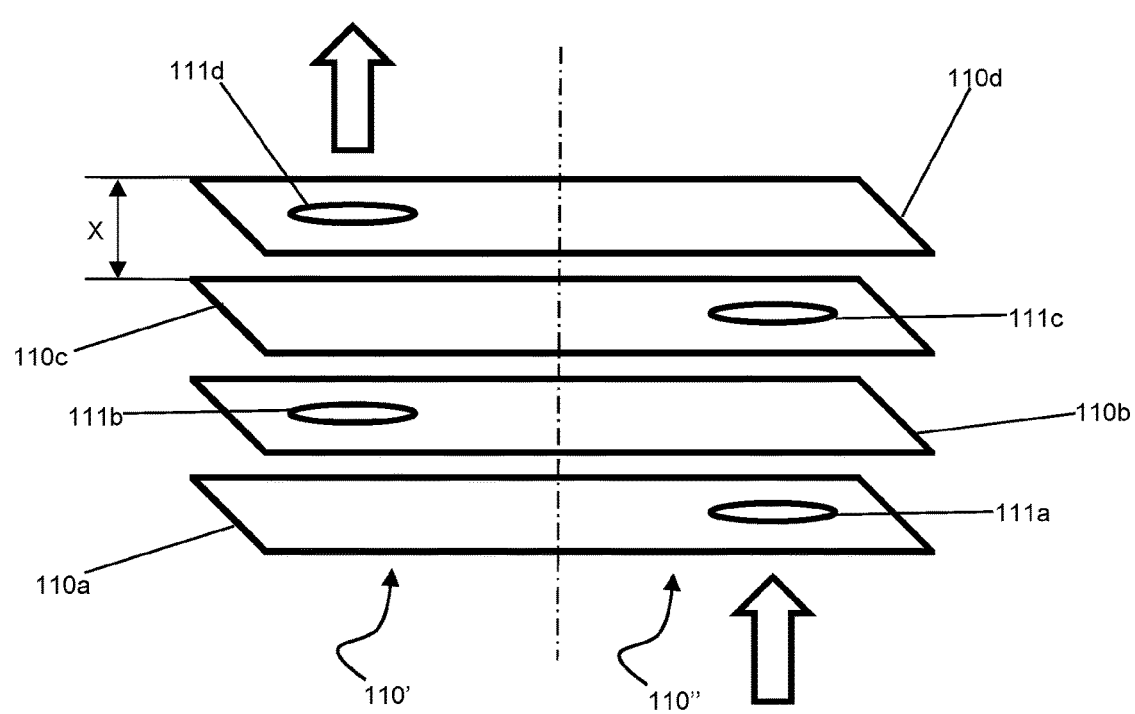
FIG. 2 shows a plurality of shelves of the device according to one embodiment of the present invention.

As shown in FIGS. 1 and 2, the device 100 according to the present invention comprises a plurality of shelves 110a, 110b, 110c, 110d. Such shelves 110a, 110b, 110c, 110d are positioned within the main body 101.

Preferably, adjacent shelves are positioned within the main body 101 at a distance X greater than or equal to 5 mm.

Preferably, the first surface 101a and the second surface 101b constitute, respectively, one shelf.

Preferably, adjacent shelves are positioned in such a way as to be parallel to each other. Preferably, adjacent shelves are positioned in such a way as to be parallel to and equidistant from each other.

Preferably, each shelf 110a, 110b, 110c, 110d has a surface that reflects, at least partially, electromagnetic waves having a wavelength of 100 nm to 400 nm. For example, each shelf 110a, 110b, 110c, 110d is made of teflon or aluminium.

Preferably, the inner surface of the main body 101 has a surface that reflects, at least partially, electromagnetic waves having a wavelength of 100 nm to 400 nm. For example, the inner surface of the main body 101 is made of teflon or aluminium.

Alternatively, the reflecting surfaces of each shelf 110a, 110b, 110c, 110d and/or of the main body 101 are made by deposition of materials that reflect, at least partially, electromagnetic waves having wavelength of 100 nm to 400 nm. The processes for depositing materials onto surfaces are known and will not be described herein.

According to the present invention, each shelf 110a, 110b, 110c, 110d is provided with at least one through hole 111a, 111b, 111c, 111d (FIG. 2).

In the following, holes formed in one same shelf will be generally identified by reference numeral 111a.

Preferably, the holes 111a formed in a respective shelf 110a have at least one of the following features:
the holes 111a have different geometric shapes;
the holes 111a are located in irregular positions on the respective shelf 110a.
The expression "holes 111a located in irregular positions on a respective shelf" means that the holes are formed in the shelf in a manner such that, considering one hole, at least two adjacent holes have different center-to-center distances.

Preferably, each shelf 110a, 110b, 110c, 110d comprises a first half-part 110' and a second half-part 110". Preferably, at least one through hole 111a is formed in the first half-part of a respective shelf 110a.

Preferably, the second half-part of each shelf 110a, 110b, 110c, 110d is solid. In other words, the second half-part of each shelf 110a, 110b, 110c, 110d has no holes.

Figure 4:
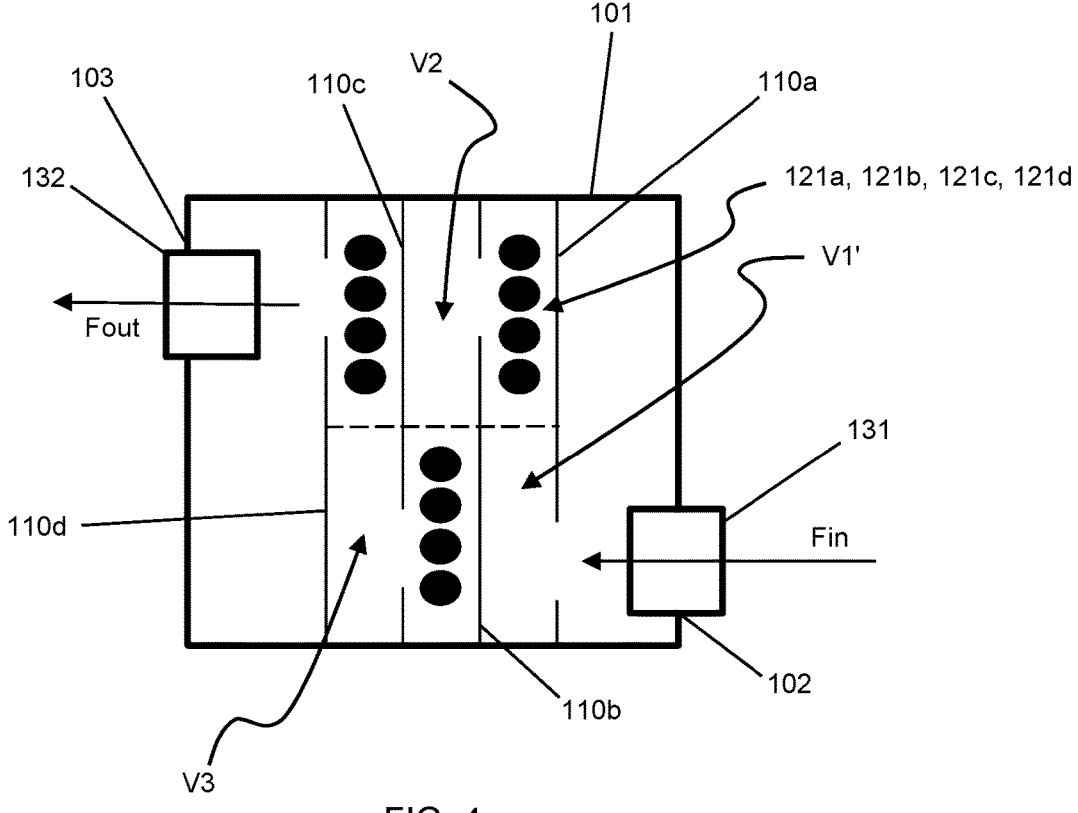
FIG. 4 is a sectional view along plane A-A of the elements shown in FIG. 1.

Preferably, as shown in FIG. 4, the shelves 110a, 110b, 110c, 110d are positioned within the main body 101 in such a way that, in a plan view, holes 111a, 111b, 111c, 111d formed in adjacent shelves 110a, 110b, 110c, 110d are mutually offset.

The Applicant observes that:
by positioning the shelves 110a, 110b, 110c, 110d at a constant distance or at different distances from each other; and/or
by making the holes 111a, 111b, 111c, 111d in adjacent shelves in such a way that, in a plan view, they are not mutually aligned and/or have different geometric shapes;

it is possible to obtain a turbulent flow within the device 100.

Figure 3:
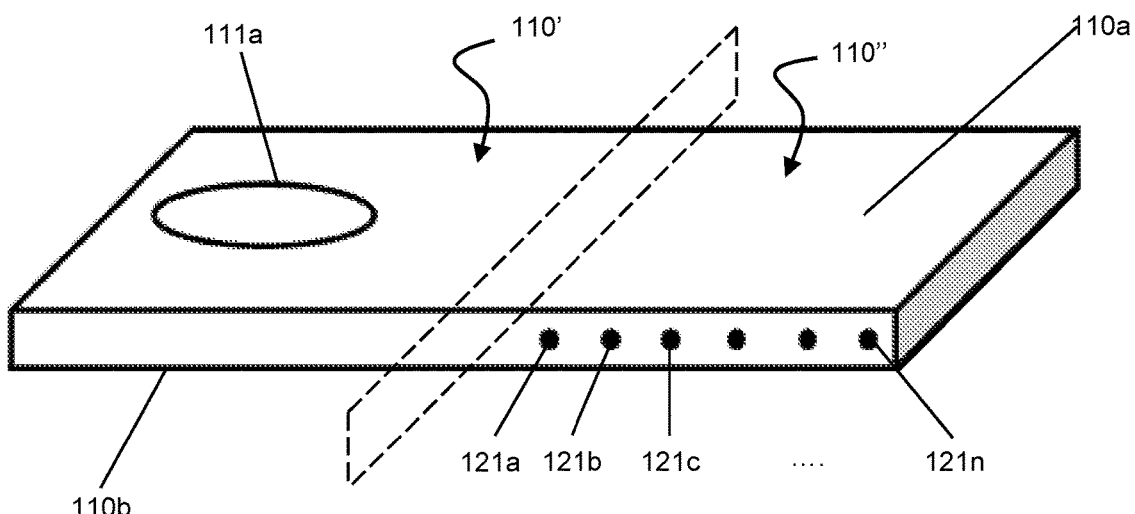
FIG. 3 shows the arrangement of a plurality of sources of electromagnetic waves relative to two adjacent shelves.

As shown in FIGS. 3 and 4, the device 100 further comprises a plurality of UV electromagnetic sources 121a, 121b, 121c, . . . , 121n. In particular, such UV electromagnetic sources 121a, 121b, 121c, . . . , 121n emit electromagnetic radiations having a wavelength of 100 nm to 400 nm. Even more preferably, such UV electromagnetic sources 121a, 121b, 121c, . . . , 121n emit UV-c electromagnetic radiations.

The UV electromagnetic sources 121a, 121b, 121c, . . . , 121n are positioned on the lateral surface of the main body 101. In particular, the UV electromagnetic sources 121a, 121b, 121c, . . . , 121n are positioned on the lateral surface of the main body 101 in such a way as to emit UV light within the main body 101.

As shown in FIGS. 3 and 4, a number N of sources of such plurality of UV electromagnetic sources 121a, 121b, 121c, . . . , 121n are interposed between two adjacent shelves 110a, 110b.

In particular, the lateral surface of the main body 101 and two adjacent shelves 110a, 110b delimit a portion of the inner volume of the main body 101. A number N of UV electromagnetic sources 121a, 121b, 121c, 121d (e.g. N=4) are positioned on the lateral surface of the main body 101 delimited by such adjacent shelves 110a, 110b. Such UV electromagnetic sources 121a, 121b, 121c, 121d generate, within the volume delimited by two parallel shelves, a UV electromagnetic field preferably having a mean intensity in excess of 5 mW/cm$^2$.

It should be noted that the first aperture 102, the second aperture 103 and each hole 111a, 111b, 111c, 111d of each shelf 110a, 110b, 110c, 110d are in fluidic communication with one another.

As shown in FIG. 4, the device 100 comprises a first fan 131, connected to the first aperture 102. The first fan 131 sucks air Fin into the main body 101. Note that the amount of air supplied into the main body 101 can be adjusted by suitably controlling the revolution speed of the first fan 131.

Figure 5:
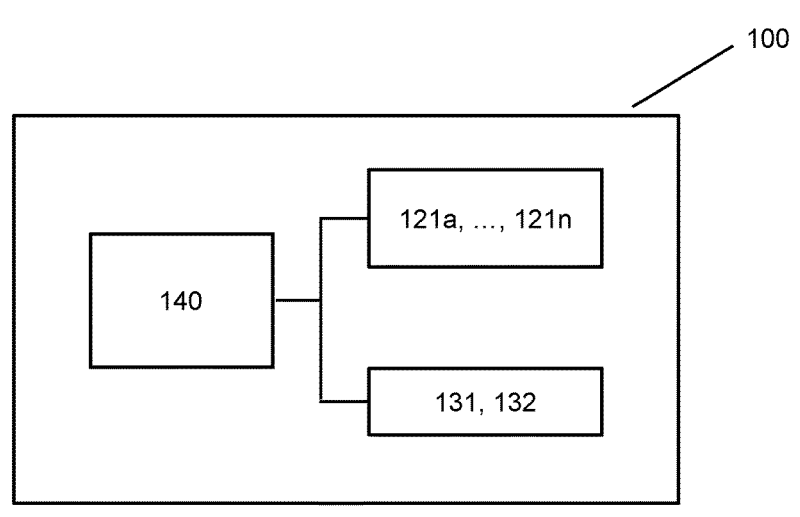
FIG. 5 is a block diagram of the device according to the present invention.

As shown in FIG. 5, the device 100 comprises a control unit 140. The control unit 140 is configured for driving each UV electromagnetic source 121a, 121b, 121c, . . . 121n and the first suction fan 131.

Preferably, the device 100 further comprises a second fan 132. The second fan 132 is connected to the second aperture 103. The first fan 131 and the second fan 132 are driven by the control unit 140, generating an air flow within said main body 101. It should be noted that by appropriately controlling the revolution speed of the first and second fans 131, 132 it is possible to adjust the velocity of the air flow Fout-Fin. Even more preferably, the first fan 131 and the second fan 132 generate an air flow Fout-Fin that, as it crosses the main body 101, moves in a turbulent manner within the main body 101.

In particular, as shown in FIG. 4, the first fan 131 and the second fan 132 (if present) generate an air flow Fout-Fin that crosses the main body 101.

In particular:
the air flow Fout-Fin is conveyed into the main body 101 by the first fan 131, positioned at the first aperture 102;
the air flow F crosses the hole(s) formed in the first half-part of the first shelf 110a and reaches the volume V1 comprised between the first shelf 110a and the second shelf 110b. As it crosses the volume V1, the air flow absorbs a first dose of UV electromagnetic waves;
the air flow Fout-Fin crosses the hole (s) formed in the first half-part of the second shelf 110b and reaches the volume V2 comprised between the second shelf 110b and the third shelf 110*c*. As it crosses the volume V2, the air flow absorbs a second dose of UV electromagnetic waves;

the air flow Fout-Fin crosses the hole (s) formed in the first half-part of the third shelf 110*c* and reaches the volume V3 comprised between the third shelf 110*c* and the fourth shelf 110*d*. As it crosses the volume V3, the air flow absorbs a third dose of UV electromagnetic waves;

the air flow Fout-Fin crosses the hole (s) formed in the first half-part of the fourth shelf 110*d* and exits the main body 101 again through the second aperture 103 or through the second fan 132 (if present) positioned at the second aperture 103.

Therefore, it should be noted that, as it crosses each volume V1, V2, V3, delimited by adjacent shelves, the air flow receives a dose of UV electromagnetic radiations. The number of shelves 110*a*, 110*b*, 110*c*, . . . 110*n* and the number of sources of UV electromagnetic waves 121*a*, 121*b*, 121*c*, . . . , 121*n* are selected in such a way as to obtain an average dose of UV electromagnetic radiation capable of reducing or deactivating bacteria and/or viruses and/or other bacterial species.

As is known, UV radiation deactivates bacteria, viruses and other microbial species by directly acting upon their DNA/RNA. In particular, UV radiation can penetrate the cell membrane and break the structure of the DNA/RNA of such bacteria, viruses and/or other microbial species.

Different pathogenic agents have different resistance to the UV electromagnetic field. In particular, in order to deactivate such bacteria, viruses and other microbial species it is necessary to provide an absorbed dose expressed by the following relation:

$$D = I*T$$

where D is the absorbed dose, measured in thousandths of Joule per square centimeter ($mJ/cm^2$); I is the intensity of the electromagnetic field I, measured in thousandths of Watt per square centimeter ($mW/cm^2$), and T is the dwell time within the electromagnetic field I, measured in seconds (s).

By way of example, below are listed the values of the doses necessary for reducing some viruses and bacteria by 99%:

as far as bacteria are concerned, in order to abate the twenty-four different strains of *Escherichia coli* it is necessary to provide a dose in the range of [2-8 $mJ/cm^2$], while the three strains of *Legionella pneumophila* require a dose in the range of [3.2-5 $mJ/cm^2$] and the two strains of *Streptococcus faecalis* require a dose in the range of [6.5-8.8 $mJ/cm^2$];

as far as viruses are concerned, in order to abate the seven strains of Poliovirus it is necessary to provide a dose in the range of [11-17 $mJ/cm^2$];

as far as protozoa are concerned, in order to abate the thirteen strains of *Cryptosporidium parvum* it is necessary to provide a dose in the range of [1-10 $mJ/cm^2$].

Figure 6:
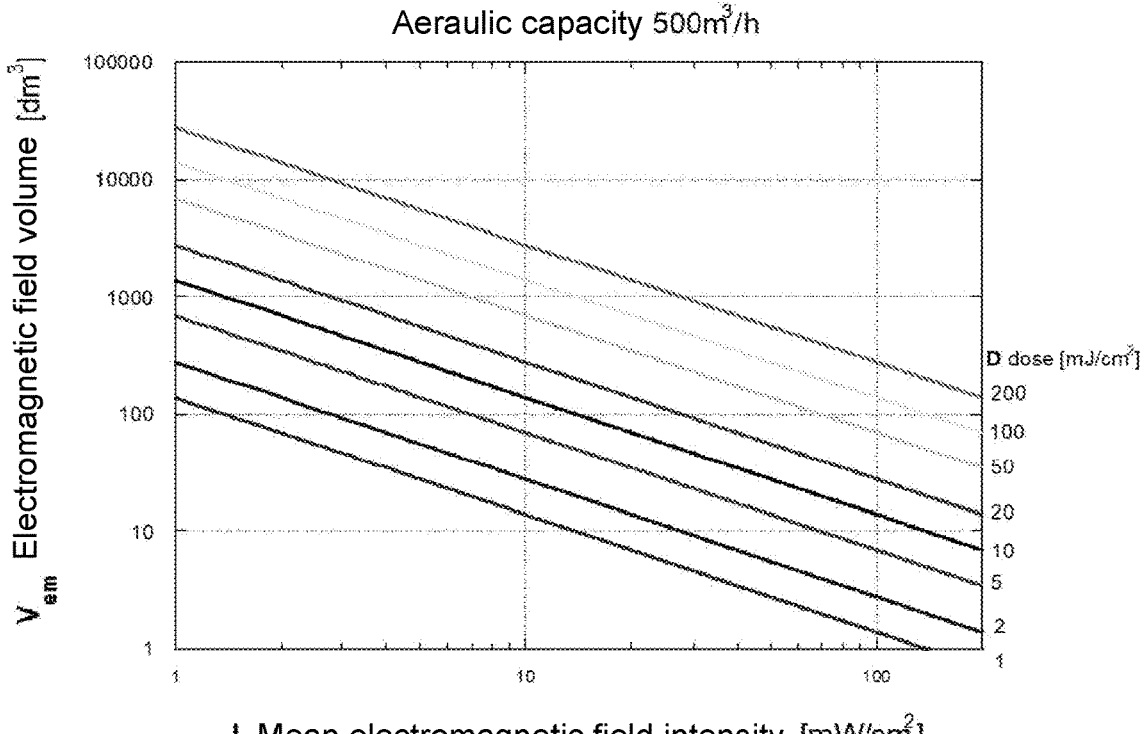
FIG. 6 is a graph showing the relationship among the mean intensity of the electromagnetic field, the air volume to be treated and the dose absorbed by such air volume for a device having an aeraulic capacity of 500 m$^3$/h.

Advantageously, with reference to FIG. 6, the dose D absorbed by an air flow Fout-Fin flowing within the main body 101 of the device 100 can be adjusted by appropriately controlling one or more of the following parameters:

air flow rate; by activating the control system 140 to drive the first fan 131 and the second fan 132 (if present) in such a way as to adjust the aeraulic capacity of the device 100 according to the environment to be treated;

number of active sources of UV electromagnetic waves between two adjacent shelves; for example, the control system 140 is configured for turning on or off a number M of the plurality of sources of UV electromagnetic waves 121*a*, 121*b*, 121*c*, 121*d*. Note that by turning on or off a number M of sources of UV electromagnetic waves it is possible to adjust the dose that is supplied to the air flow through the main body of the device 100;

mean intensity of the UV electromagnetic field generated by the sources of UV electromagnetic waves 121*a*, 121*b*, 121*c*, 121*d* interposed between adjacent shelves 110*a*, 110*b*. For example, by means of the control system 140 it is possible to control the power supplied to each source of UV electromagnetic waves 121*a*, 121*b*, 121*c*, 121*d*.

Figure 7:
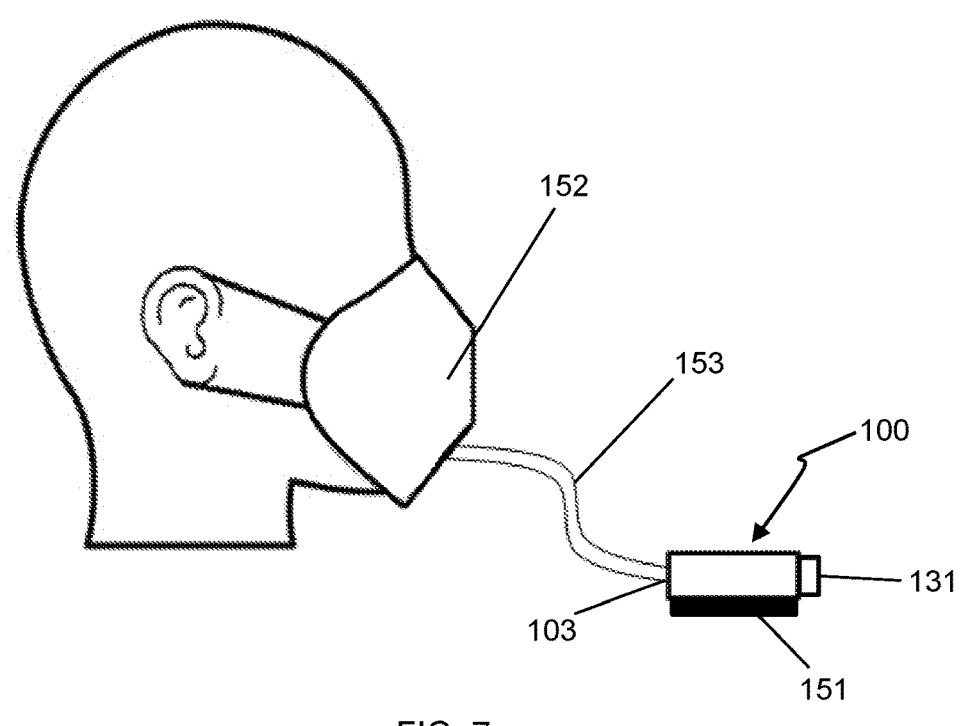
FIG. 7 shows a second embodiment of the device according to the present invention.
Figure 8:
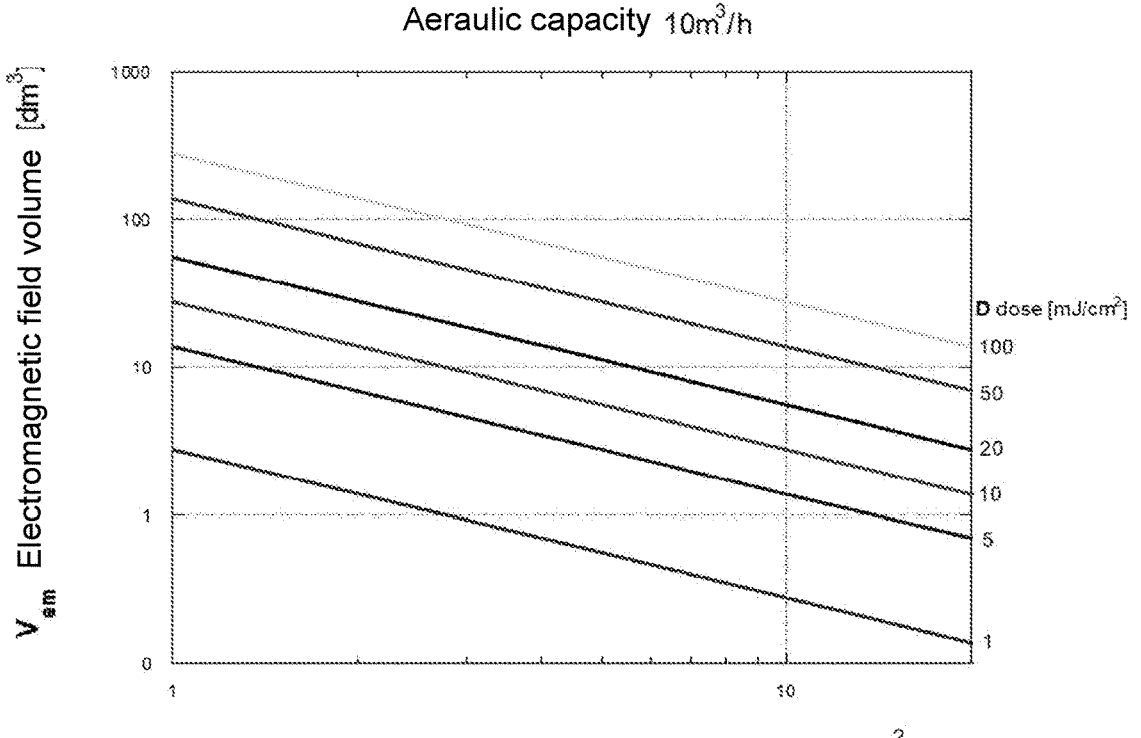
FIG. 8 is another graph showing the relationship among the mean intensity of the electromagnetic field, the air volume to be treated and the dose absorbed by such air volume for the device of FIG. 7.

With reference to FIGS. 5, 7 and 8, according to a preferred embodiment of the invention the device 100 further comprises:

a battery 151 adapted to supply power to the first suction fan 131, each UV electromagnetic source 121*a*, 121*b*, 121*c*, . . . , 121*n* and the control unit 140.

a face mask 152 adapted to cover the mouth and/or the nose of a user.

a flexible hose 153 provided with a first end and a second end.

The first end of the flexible hose 153 is connected to the second aperture 103 of the main body 101; the second end of the flexible hose 153 is connected to the face mask 152.

It should be noted that, according to this embodiment, the device 100 can be used as a personal sanitization device.

Preferably, the first suction fan 131 is configured for taking in an air volume greater than or equal to 500 $m^3/h$.

Preferably, each UV electromagnetic source 121*a*, 121*b*, 121*c*, . . . , 121*n* can provide an average dose of 1 to 200 $mJ/cm^2$.

According to the present invention, the main body 101 of the device 100 preferably has a minimum volume $V_{em}$ given by the following relation:

$$V_{em} = D \frac{1}{I} nV$$

where D is the abatement dose necessary for abating a microbiological species by 99%, I is the mean intensity of the electromagnetic field, and nV is the aeraulic capacity of the device 100.

In other words, the minimum volume $V_{em}$ containing the electromagnetic field necessary for deactivating/reducing a given bacterial species (or biological particulate matter) is directly proportional to the dose necessary for neutralizing that particular bacterial species (or biological particulate matter). Preferably, the minimum volume $V_{em}$ containing the electromagnetic field necessary for deactivating/reducing a given bacterial species (or biological particulate matter) is directly proportional to the aeraulic capacity of the device 100 (i.e. directly proportional to the air flow Fout-Fin within the main body 101) and inversely proportional to the mean intensity of the electromagnetic field generated by the plurality of sources of UV electromagnetic waves 121*a*, 121*b*, 121*c*, 121*d*.

It should be noted that, considering a device 100 suitable for abating a plurality of microbiological species, the dose D corresponds minimum dose necessary for abating that microbiological species which has the highest resistance to radiations (i.e. that microbiological species which requires the highest dose). In other words, the dose D necessary for calculating the minimum volume $V_{em}$ corresponds to the highest dose D that can be delivered by the device 100, with equal aeraulic capacity nV.

The Applicant observes that, advantageously, the intensity of the electromagnetic field emitted by each one of the sources of UV electromagnetic waves 121a, 121b, 121c, 121d is controlled by controlling both the number of sources and the current intensity supplied to each source of UV electromagnetic waves 121a, 121b, 121c, 121d. By way of example, assuming that the device 100 is to be installed in a room for treating air-borne pathogenic agents sensitive to a dose in the range of 2-8 mJ/cm$^2$, the device 100 may have the following specifications (with reference to the graph of FIG. 6):

an aeraulic capacity (i.e. the volumetric flow rate of the device 100) of 500 m$^3$/h;

a total mean intensity of the UV electromagnetic field within the main body 101 of 10 mW/cm$^2$;

a maximum dose of UV electromagnetic waves of 10 mJ/cm$^2$;

a minimum volume of the main body 101 of 120 cm$^3$.

Assuming that the device 100 is to be used as a personal air sanitization device (FIG. 7) suitable for treating air-borne pathogenic agents sensitive to a dose in the range of 2-20 mJ/cm$^2$, the device 100 may have the following specifications (with reference to the graph of FIG. 8):

an aeraulic capacity (i.e. the volumetric flow rate of the device 100) of 10 m$^3$/h;

a total mean intensity of the UV electromagnetic field within the main body 101 of 10 mW/cm$^2$;

a maximum dose of UV electromagnetic waves of 20 mJ/cm$^2$;

a minimum volume of the main body 101 of 8 cm$^3$.

As aforementioned, according to one embodiment of the present invention the main body 101 has a cylindrical shape.

Figure 9:
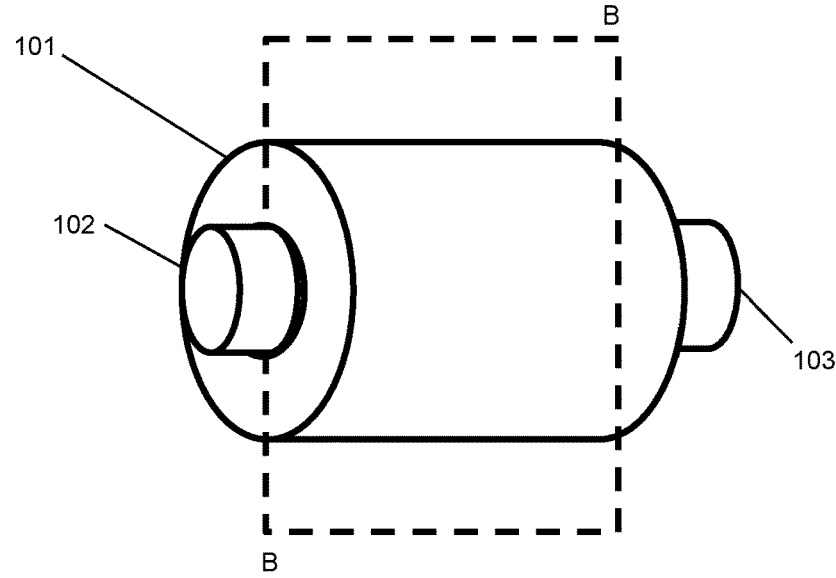
FIG. 9 shows a device according to a further embodiment of the present invention.
Figure 10:
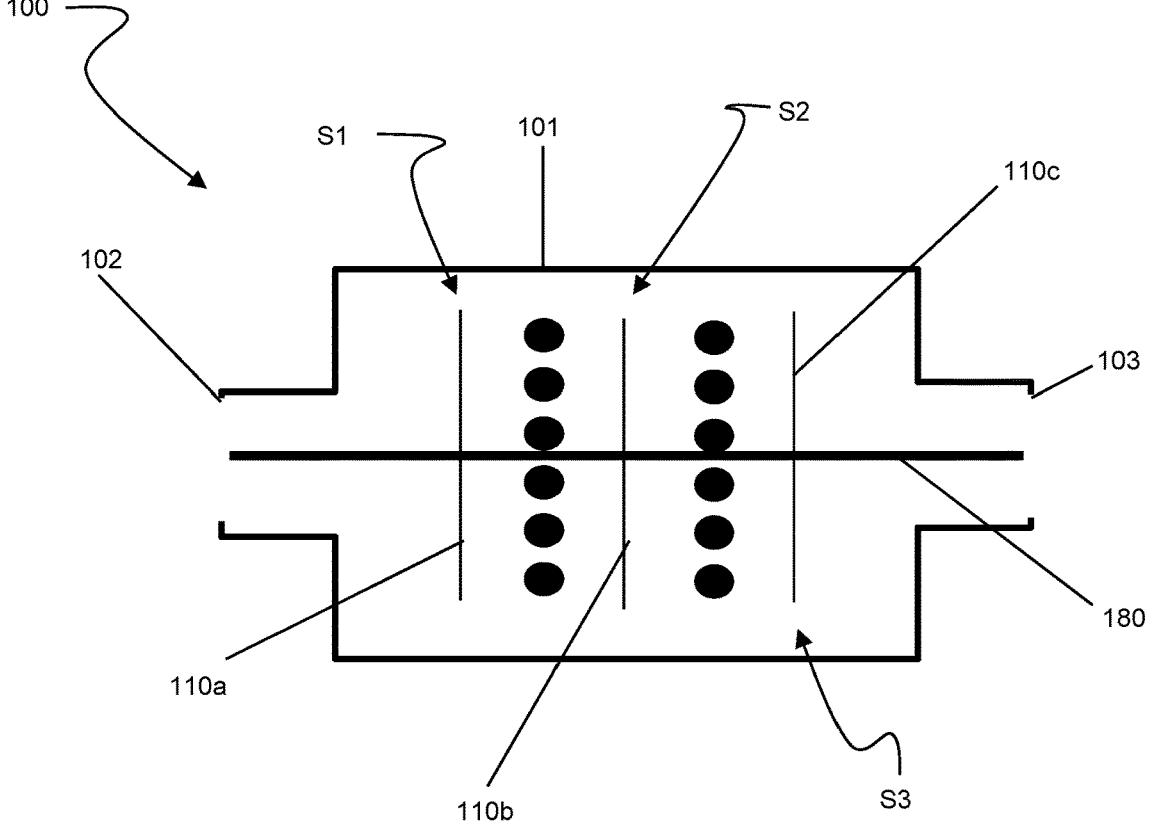
FIG. 10 is a schematic sectional view along plane B-B of the device of FIG. 9.

According to such an embodiment, the first aperture 102 and the second aperture 103 are preferably aligned along the longitudinal axis Y-Y of the main body 101 (FIG. 9).

Preferably, the device 100 further comprises a fixing rod 181. The fixing rod 181 is positioned along the longitudinal axis Y-Y. In particular, the fixing rod 181 is fixed, at its ends, to the first aperture 102 and to the second aperture 103 in any known manner (e.g. by means of suitable supporting arms—not shown—welded to the lateral surface of the first aperture 102 and second aperture 103).

Preferably, each shelf 110a, 110b, 110c is a circular shelf, the diameter of which is smaller than the diameter of the main body 101.

Preferably, each shelf 110a, 110b, 110c is fixed to the fixing rod 181. For example, each shelf 110a, 110b, 110c has a respective fixing hole at its center; each shelf 110a, 110b, 110c is keyed onto the fixing rod 181.

Preferably, such shelves 110a, 110b, 110c are fixed to the fixing rod 181 in such a way as to be parallel to each other. Even more preferably, such shelves 110a, 110b, 110c are fixed to the fixing rod 181 in such a way as to be parallel to and equidistant from each other.

It should be noted that, when such shelves 110a, 110b, 110c are positioned in the main body 101, respective spaces S1, S2, S3 are created between the outer perimeter of each shelf 110a, 110b, 110c and the inner surface of the main body 101. Preferably, such spaces S1, S2, S3 have a crown shape, even more preferably a circular crown shape.

Preferably, the first fan 131 and the second fan 132 (if present) generate an air flow Fout-Fin that, as it crosses the main body 101, moves in a turbulent manner within the main body 101.

The present invention offers some important advantages.

Advantageously, many different viruses and/or bacteria can be abated by directly controlling the velocity of the air flow within the device 100.

Advantageously, it is possible to set up the control system 140 for executing air sanitization cycles in order to abate different viruses and/or bacteria that may be present in a room.

Advantageously, the device 100 has a modular structure that allows the construction of devices suitable for treating different air amounts.

The invention claimed is:

1. A device (100) for abating microbiological components present in an air flow, comprising:

a main body (101), said main body (101) being provided, on its surface, with a first aperture (102) and a second aperture (103);

a plurality of shelves (110a, 110b, 110c, 110d) positioned within said main body (101), each shelf (110a, 110b, 110c, 110d) being provided with at least one through hole (111a, 111b, 111c, 111d);

a plurality of UV electromagnetic sources (121a, 121b, 121c, . . . , 121n) arranged between said shelves so as to emit UV light within said main body (101);

a first fan (131), connected to said first aperture (102) and adapted to suck air into said main body (101);

a control unit (140) configured for driving said plurality of UV electromagnetic sources (121a, 121b, 121c) and said suction fan (131);

wherein said first aperture (102) and said second aperture (103) and each hole (111a, 111b, 111c, 111d) of each shelf (110a, 110b, 110c, 110d) are in fluidic communication;

wherein said main body (101) has a minimum volume Vem given by the following relation:

$$V_{em} = D\frac{1}{I}nV$$

where D is the abatement dose necessary for abating a microbiological species by 99%, I is the mean intensity of the electromagnetic field of said plurality of UV electromagnetic sources (121a, 121b, 121c), and nV is the aeraulic capacity of the device (100).

2. The device (100) according to claim 1, wherein said plurality of holes (111), formed in a respective shelf (110), have at least one of the following features:

the holes (111) have different geometric shapes;

the holes (111) are located in irregular positions on the respective shelf (110).

3. The device (100) according to claim 1, wherein each shelf comprises a first half-part and a second half-part;

wherein said at least one through hole is formed in said first half-part, while said second half-part is solid.

4. The device (100) according to claim 1, in a plan view, holes (111a, 111b, 111c, 111d) formed in adjacent shelves (110a, 110b, 110c, 110d) are mutually offset.

5. The device (100) according to claim 4, wherein each shelf (110a, 110b, 110c, 110d) has a surface that reflects, at least partially, electromagnetic waves having a wavelength of 100 nm to 400 nm.

6. The device (100) according to claim 5, wherein each shelf (110a, 110b, 110c, 110d) is made of teflon or aluminium.

7. The device (100) according to claim 1, wherein said main body (101) is a box-shaped body having a first surface (101*a*) and a second surface (101*b*) that are substantially parallel to each other;

wherein said first aperture (102) is formed in said first surface (101*a*) and said second aperture (103) is formed in said second surface (101*b*).

8. The device (100) according to claim 1, wherein adjacent shelves are positioned at a distance (X) greater than or equal to 5 mm.

9. The device (100) according to claim 1, wherein said device (100) further comprises a second fan (132) connected to said second aperture (103);

wherein said first fan (131) and said second fan (132) are driven by said control unit (140), generating within said main body an air flow at a controllable speed.

10. The device (100) according to claim 1, wherein said device (100) further comprises:

a battery (151) adapted to supply power to said first fan (131), said plurality of UV electromagnetic sources (121*a*, 121*b*, 121*c*, . . . , 121*n*) and said control unit (140);

a face mask (152) adapted to cover the mouth and/or the nose of a user;

a flexible hose (153) provided with a first end and a second end, wherein:

said first end is connected to said second aperture (103);

said second end is connected to said face mask (152).

* * * * *